(12) United States Patent
Mankin (10) Patent No.: US 12,083,049 B2
(45) Date of Patent: Sep. 10, 2024

(54) ASSEMBLY FOR THE POSITIONING AND POSITION DETECTION OF A DEFORMABLE LOAD-BEARING PLATE

(71) Applicant: PHYSIK INSTRUMENTE (PI) GMBH & CO. KG, Karlsruhe (DE)

(72) Inventor: Erik Mankin, Karlsruhe (DE)

(73) Assignee: PHYSIK INSTRUMENTE (PI) GMBH & CO. KG, Karlsruhe (DE)

( * ) Notice: Subject to any disclaimer, the term of this patent is extended or adjusted under 35 U.S.C. 154(b) by 741 days.

(21) Appl. No.: 17/285,239

(22) PCT Filed: Oct. 9, 2019

(86) PCT No.: PCT/EP2019/077336
§ 371 (c)(1),
(2) Date: Apr. 14, 2021

(87) PCT Pub. No.: WO2020/078791
PCT Pub. Date: Apr. 23, 2020

(65) Prior Publication Data
US 2021/0369529 A1    Dec. 2, 2021

(30) Foreign Application Priority Data

Oct. 19, 2018  (DE) .......................... 102018126022.9

(51) Int. Cl.
*A61G 13/04*    (2006.01)
*A61B 6/04*    (2006.01)
(Continued)

(52) U.S. Cl.
CPC ......... *A61G 13/04* (2013.01); *A61G 13/0018* (2013.01); *B25J 9/0075* (2013.01);
(Continued)

(58) Field of Classification Search
CPC ................ A61G 13/04; A61G 13/0018; A61G 2203/32; A61G 2203/34; B25J 9/1638;
(Continued)

(56) References Cited

U.S. PATENT DOCUMENTS 8,442,677 B2 * 5/2013 Shoham ................ B25J 9/1623
700/250
9,240,045 B2 * 1/2016 Noshi .................. A61B 6/5276
(Continued)

FOREIGN PATENT DOCUMENTS

AT         502426 A1    3/2007  ................ B25J 9/10
CN    105126261 A  * 12/2015  ........... A61G 13/009
(Continued)

OTHER PUBLICATIONS

CN-105126261-A Eng (Year: 2015).*
(Continued)

*Primary Examiner* — Justin C Mikowski
*Assistant Examiner* — Amanda L Bailey
(74) *Attorney, Agent, or Firm* — Bodner & Bodner, PLLC; Christian P. Bodner; Gerald T. Bodner (57) ABSTRACT

The invention relates to an assembly for the positioning and position detection of a deformable load-bearing plate, having a driving parallel kinematics system with a plurality of drive legs, wherein the load-bearing plate forms a constituent part of the driving parallel kinematics system or is fixed rigidly on a platform thereof, a reference parallel kinematics system with a substantially deformation-free reference plate which is formed by the platform of the reference parallel kinematics system or is fixed rigidly thereto and which is positioned underneath the load-bearing plate, and a plurality of reference legs, a sensor assembly which comprises a plurality of leg length measurement devices arranged in the reference legs and also a plurality of distance sensors
(Continued)

arranged on the reference plate for point-wise or region-wise detection of the distance of the reference plate from the load-bearing plate, and a position-calculating unit which is connected at the input side to the leg length measurement devices and to the distance sensors and which processes the output signals of the leg length measurement devices and distance sensors to give a position map of the load-bearing plate.

19 Claims, 5 Drawing Sheets

(51) Int. Cl.
    *A61G 13/00*      (2006.01)
    *B25J 9/00*      (2006.01)
    *B25J 13/08*      (2006.01)
    *B25J 19/00*      (2006.01)
    *G01B 21/16*      (2006.01)

(52) U.S. Cl.
    CPC ........... *B25J 13/085* (2013.01); *B25J 13/089* (2013.01); *B25J 19/0016* (2013.01); *G01B 21/16* (2013.01); *A61B 6/0487* (2020.08); *A61G 2203/40* (2013.01)

(58) Field of Classification Search
    CPC ........ B25J 9/1623; B25J 13/086; B25J 9/003; G01B 21/16
    See application file for complete search history.

(56) References Cited

U.S. PATENT DOCUMENTS

| | | | | |
|---|---|---|---|---|
| 9,757,658 | B1 | 9/2017 | Kaufmann | |
| 2002/0081008 | A1* | 6/2002 | Wollenweber | A61B 6/547 382/294 |
| 2003/0005786 | A1* | 1/2003 | Stuart | B25J 17/0266 409/235 |
| 2008/0289106 | A1* | 11/2008 | Beyer | A61B 6/5276 5/601 |
| 2009/0139032 | A1* | 6/2009 | Bak | A61B 6/5276 5/658 |
| 2010/0034435 | A1* | 2/2010 | Kariv | A61B 6/5276 5/601 |
| 2010/0122602 | A1* | 5/2010 | Marcroft | B25J 17/0216 901/18 |
| 2012/0076269 | A1* | 3/2012 | Roberts | A61N 5/1049 378/65 |
| 2016/0288317 | A1* | 10/2016 | Gheorghe | B25J 9/003 |
| 2018/0110486 | A1* | 4/2018 | Suga | A61B 34/71 |
| 2018/0116885 | A1* | 5/2018 | St. John | A61G 7/005 |
| 2018/0228678 | A1* | 8/2018 | Sauser | A61G 7/05776 |
| 2019/0301144 | A1* | 10/2019 | Kean | E02F 9/265 |

FOREIGN PATENT DOCUMENTS

| | | | | |
|---|---|---|---|---|
| CN | 106476013 | A * | 3/2017 | ............ B25J 9/1602 |
| DE | 102017104189 | A1 | 8/2018 | ............ B25J 11/00 |
| KR | 101176414 | B1 | 8/2012 | ............ B25J 17/00 |
| WO | WO9928097 | A1 | 6/1999 | ................ B25J 9/16 |
| WO | WO-2009073027 | A1 * | 6/2009 | ............ A61G 15/02 |
| WO | WO2018045463 | A1 | 3/2018 | ............... B23Q 3/00 |
| WO | WO-2018158056 | A1 * | 9/2018 | ............ B25J 13/088 |

OTHER PUBLICATIONS

CN-106476013-A Eng (Year: 2017).*
WO-2009073027-A1 Eng (Year: 2009).*
WO-2018158056-A1 Eng (Year: 2018).*
The Notification Concerning Transmittal of International Preliminary Report on Patentability (Chapter I of the Patent Cooperation Treaty), in English, dated Apr. 29, 2021, which was issued by the International Bureau of WIPO in Applicant's corresponding international PCT application having Serial No. PCT/EP2019/077336, filed on Oct. 9, 2019.
English translation of the International Preliminary Report on Patentability (Chapter I of the Patent Cooperation Treaty), dated Apr. 14, 2021, which was issued by the International Bureau of WIPO in Applicant's corresponding international PCT application having Serial No. PCT/EP2019/077336, filed on Oct. 9, 2019.
Written Opinion of the International Searching Authority, in English, dated Jan. 15, 2020, which was issued by the International Bureau of WIPO in Applicant's corresponding international PCT application having Serial No. PCT/EP2019/077336, filed on Oct. 9, 2019.
International Search Report, in English, dated Jan. 15, 2020, which was issued by the International Bureau of WIPO in Applicant's corresponding international PCT application having Serial No. PCT/EP2019/077336, filed on Oct. 9, 2019.
An Office Action (in German), dated Jul. 8, 2019, issued by the German Patent Office for Applicant's corresponding German Patent Application No. DE102018126022.9, filed Oct. 19, 2018.

* cited by examiner

ASSEMBLY FOR THE POSITIONING AND POSITION DETECTION OF A DEFORMABLE LOAD-BEARING PLATE

The invention relates to an assembly for the positioning and position detection of a deformable load-bearing plate, having a driving parallel kinematics system with a plurality of drive legs, wherein the load-bearing plate forms a constituent part of the driving parallel kinematics system or is fixed rigidly on a platform thereof.

So-called parallel kinematics system, in particular hexapods or else Stewart platforms, have been employed for some time for the highly accurate positioning of parts, in particular in production processes but also of measurement systems as well as of patients in the context of imaging methods or radiotherapy. Recently, the range of application of such assemblies has greatly expanded, and the accuracy requirements are very high for a number of fields of application.

The document WO 1999/028097 A1 discloses a method for calibrating a parallel kinematics system, which is based on the evaluation of sensor data regarding the distance of the actual position from a reference position of the platform. The document US 2018/0110486 A1 shows an application of a generic parallel kinematics system for positioning a patient table of a medical diagnostic or therapy system.

Especially in the precise positioning of patients in highly accurate imaging diagnostic systems and in radiotherapy, respectively, or in high-load applications, deformations of the load-bearing plate are no longer negligible and need to be taken into account for fulfilling the accuracy requirements existing in the corresponding context.

The invention is therefore based on the task to propose an improved assembly for the positioning and position detection of a load-bearing plate, which assembly allows the needs of high accuracy requirements to be met.

This task is solved by an assembly having the features of claim 1. Appropriate further developments of the idea of the invention are the subject matter of the dependent claims.

An idea of the invention is to provide, in addition to the driving parallel kinematics system, a reference parallel kinematics system with a substantially deformation-free reference plate which is formed by the platform of the reference parallel kinematics system or is fixed rigidly thereto and which is positioned underneath the load-bearing plate, and with a plurality of reference legs. The assumed deformation freedom of the reference plate of this reference parallel kinematics system is in particular guaranteed by a realization having high rigidity (due to suitable material and/or suitable interior structure and/or suitable geometry) and by keeping the reference plate mostly free from introduced forces.

Furthermore, according to the invention, a sensor assembly is provided which comprises a plurality of leg length measurement devices arranged in the reference legs and also a plurality of distance sensors arranged on the reference plate for local (point-wise or region-wise) detection of the distance of the reference plate from the load-bearing plate. With regard to the almost rigid reference plate, the sensor assembly obtains a plurality of sensor signals for describing the spatial position of the load-bearing plate (potentially deformed by the carried load).

Finally, the proposed assembly comprises a position-calculating unit which is connected at the input side to the leg length measurement devices and to the distance sensors, and which processes the output signals of the leg length measurement devices and the distance sensors to give a quantity of three-dimensional coordinates, resulting in a position map of the load-bearing plate. The thus obtained exact image of the spatial contour of the load-bearing plate can provide input signals for correction devices which, for example, reposition the load-bearing plate or can actively compensate the load-conditioned deformations of the load-bearing plate, possibly by utilizing a static overdeterminedness in case of an optional use of surplus or "redundant" legs. On the other hand, the present (and uncompensated) deformations may be computationally taken into account for the signal evaluation of an associated imaging examination system or for controlling a processing or therapy system. For example, an adaptation of the beam guidance may be performed in radiotherapy.

In one realization of the invention, the reference parallel kinematics system is provided as a separate constructional unit in addition to the driving parallel kinematics system, and its platform is formed as a load-free platform. In this realization, the assembly comprises means for laterally aligning the reference plate with respect to the platform of the driving parallel kinematics system, wherein the means for laterally aligning comprise in particular interacting slide agents at the reference plate and the platform of the driving parallel kinematics system, and a laterally acting tension spring device.

In an alternative configuration, the reference parallel kinematics system is simultaneously formed by the driving parallel kinematics system, wherein the platform of the driving parallel kinematics system is significantly smaller than the load-bearing plate, and consequently is to be considered to be approximately free from deformation. In this case, the reference plate is provided as an additional element to the small platform ("nacelle") of the driving/reference parallel kinematics system and is connected both to the platform of the parallel kinematics system and the load-bearing plate.

From the current point of view, in a realization which is especially important and can be practically used in a versatile manner, the driving parallel kinematics system and/or the reference parallel kinematics system have/has a hexapod which comprises at least six length-variable legs and, as the platform, have/has a nacelle, and in particular also a base plate. Basically, however, the invention can also be used advantageously with other types of parallel kinematics systems, and can also open up such fields of application in which high accuracy requirements are to be fulfilled.

While a hexapod—as already suggested by the name—usually has six legs, realizations van be advantageous in the context of the invention, in which the driving parallel kinematics system comprises more than six variable drive legs and/or in which the reference parallel kinematics system comprises more than six reference legs, with leg length measurement devices being provided in each of them.

The use of surplus or "redundant" reference legs enables a refined evaluation and/or exploitation of the position measurement results on the control side, improved fault correction or technical fault recognition in the drive legs and/or reference legs, resulting as a whole in more accurate and more reliable posture measurement of the reference plate and thus in a more accurate and more reliable positioning of the load-bearing plate. Posture is in this case to be understood as the combination of position and orientation of a rigid object or body, e.g. the reference plate, in the three-dimensional space.

The provision of "redundant" drive legs, on the one hand, facilitates the recognition of technical disturbances, if the drive legs are equipped with length measurement devices.

On the other hand, the parallel kinematics system is thereby statically overdetermined so that apart from positioning the load-bearing plate, a targeted deformation thereof may also be caused. These targeted deformations may serve the purpose, for example, of counteracting load-conditioned deformations. Positionings and deformations of the load-bearing plate can be tracked and iteratively refined by the measurements of the sensor assembly of the reference parallel kinematics system. When deformations are caused by overdetermined kinematics, the measurement of the leg forces is recommended at least via monitoring the electric currents of the leg drives; it is furthermore advantageous, when the possibility is given to switch "redundant" legs to powerless.

In the context of the invention, the leg length measurement devices in the legs of the reference parallel kinematics system and the distance sensors on the reference plate preferably are realized as absolute value sensors. Basically, an implementation of the invention is also possible with relative value sensors, this, however, would require additional calibration steps in each case and would make the realization more complex.

In the normal case, the distance sensors can be arranged at the corner points of at least one equilateral triangle or rectangle, in particular in a regular arrangement formed of a plurality of equilateral triangles or rectangles. It goes without saying that other polygonal arrangements of the distance sensors (such as on the points of one or more hexagon/s) are also possible, if the requirements of the specific case of application thus are met better.

In further realizations, the distance sensors on the reference plate are arranged to be position-variable such that the positioning thereof can be adjusted in coordination with the mechanical properties of the load-bearing plate and optionally with a special load configuration. This indeed requires a more complex structure of the reference plate with corresponding adjustable retainers or guides for the distance sensors, but enables a more flexible adaptation thereof to diverse situations of application.

In an important application of the assembly, the load-bearing plate is formed as a patient table of a medical diagnostic and therapy system. In a further important case of application, the load-bearing plate is formed as a heavy load platform as part of a technical measurement and processing system. It goes without saying, that the invention can also be used with a special advantage in further fields of application, in which relatively large and at the same time extensive loads are placed on a correspondingly expanded load-bearing plate.

In a practically significant extended configuration, the assembly has a position tracking unit connected to the output of the position calculating unit at the input side, and the position map of the load-bearing plate receives representative data, and based on this data causes, where appropriate, an iterative position tracking of the load-bearing plate in the loaded and deformed state thereof.

With regard to the configuration with "redundant" or surplus legs mentioned further above, the position tracking unit may in this case have at least one output connected to one of the surplus drive legs of the driving parallel kinematics system for the length variation thereof.

If a parallel kinematics system is overdetermined (for example, a "hexapod" having seven legs), a posture is defined by specifying exactly 6 leg lengths. If a "redundant" leg is then moved in addition, the result will be a tension of the nacelle. The occurring maximum forces depend on the maximally realizable leg forces, the elasticity of the kinematics system and finally also on the mechanical load-bearing capacity/stability of the kinematics system. Very large leg forces and even tensions of unknown magnitude may occur in mechanics, which can have serious consequences. It is therefore advantageous for force measurement devices to be provided in redundant legs in order to be able to detect such states in a timely manner and to counteract them.

Incidentally, advantages and expedient functionalities of the invention will result from the following description of exemplary embodiment on the basis of the Figures. Shown are in the Figures to the exemplary embodiments.

Figure 1:
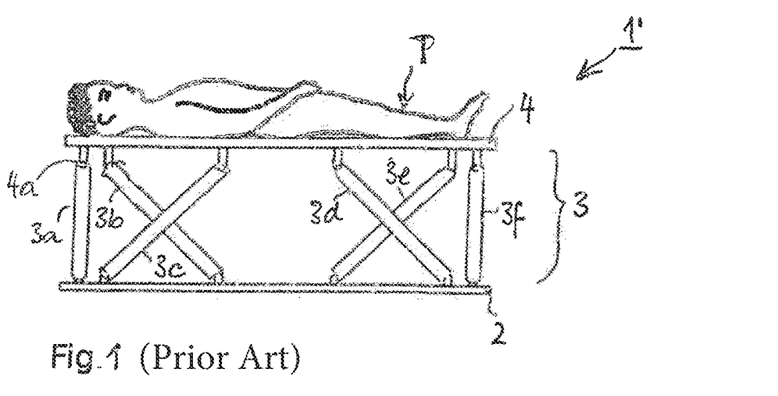
FIG. 1 a side view of a patient table driven by a parallel kinematics system in a known structure, FIGS. 2A and 2B a perspective representation as well as a side view of a patient table with an assembly according to the invention for the positioning and position detection, FIG. 3 a perspective representation of the base plate and the reference parallel kinematics system of the assembly according to FIGS. 2A and 2B, FIGS. 4A, 4B and 4C a perspective bottom view as well as two side views of the reference plate and the load-bearing plate for explaining the connection arrangement between them, FIG. 5 a perspective representation of a further structure detail of the reference plate, FIG. 6 a side view of the reference parallel kinematics system, FIG. 7 a side view of a modified embodiment of the patient table shown in FIGS. 2A and 2B, FIG. 8 a perspective representation of the reference plate of the patient table according to FIG. 7, FIGS. 9, 10A and 10B schematic representations for explaining the operating mode of the position sensor system in a further exemplary assembly.

FIG. 1 shows the structure of a patient table 1' known per se for being used with imaging diagnostic devices, such as an X-ray or computer tomography system, or for being used in radiotherapy, with a patient P lying thereon. The patient table represents a generic assembly and comprises a base plate 2 and a parallel kinematics system 3, to which the load-bearing plate 4 serving as a patient support, and six drive legs 3a to 3f belong.

The parallel kinematics system 3 is of the hexapod type. The drive legs 3a to 3f are connected at both ends to the base plate 2 via (not designated) ball joints, on the one hand, and to the load-bearing plate 4, on the other. At the linking points of the drive legs to the load-bearing plate, so-called leg shafts are provided, of which only one is designated here in an exemplary manner by numeral 4a, and the structure of which—just as the structure of the hexapod 3 as a whole—is assumed to be known.

Functionally, the load-bearing plate 4 corresponds to the so-called nacelle of a conventional hexapod, but differs from this nacelle, which is regarded as a rigid body, by the deformability thereof, and that it consequently cannot have a so-called posture allocated, and its extension in space cannot be described (like in a rigid body) by six posture parameters.

Due to the weight of the patient, a deformation of the hexapod and primarily of the load-bearing plate 4 occurs resulting in a shifting of the patient but also of the mentioned linking points. Because of that, the load-bearing plate rotates also in space and shifts in a Cartesian coordinate system. This deformation and spatial rotation, in turn, falsify the position signals obtained from the drive of the load-bearing plate, which position signals are included in the evaluation of the data obtained by the imaging diagnostic system, and thus ultimately results in a reduced accuracy of these data.

Figure 2A:
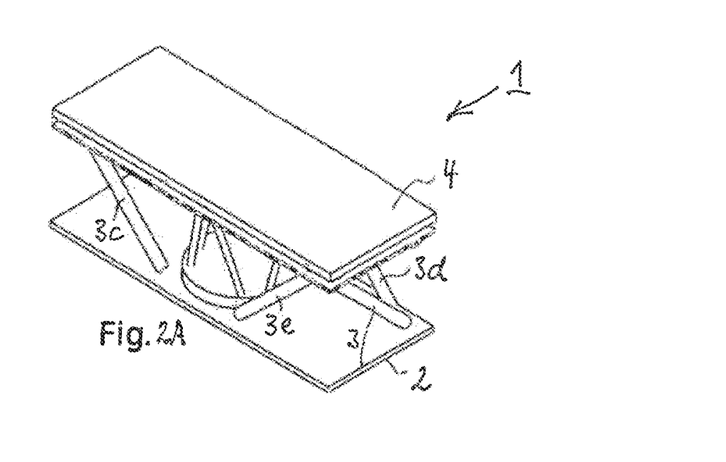
Figure 2B:
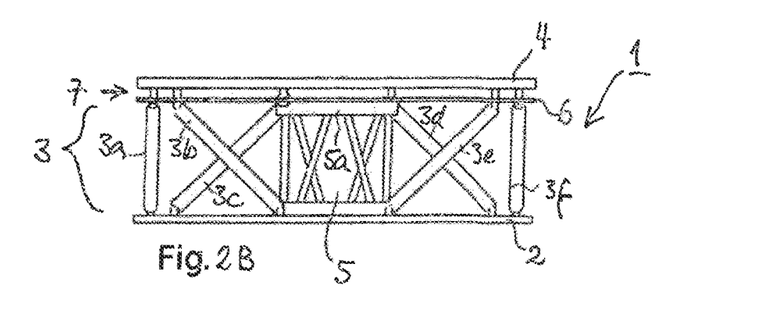

FIGS. 2A and 2B show a patient table 1 as an example of an assembly according to the invention in a perspective top view and side view, respectively. The assembly is similar to the known assembly represented in FIG. 1, and functionally or widely corresponding parts are designated by the same reference numerals as in FIG. 1.

In addition to the driving kinematics system, a reference kinematics system 5 with a nacelle 5a and an attached reference plate 6 is provided in the assembly 1, representing the mechanical basis for a highly accurate position detection taking into account load-conditioned deformations, and the positioning of the patient based on that. The sensor system and evaluation technique furthermore belonging thereto are not illustrated in FIGS. 2A and 2B, and the legs (hereinafter: reference legs) of the reference parallel kinematics system 5 are not designated individually here.

As can be recognized in FIG. 2B, the drive legs 3a to 3f in the exemplary assembly 1 according to the invention are hinged to the lower side of the reference plate 6, consequently not directly at the load-bearing plate 4, as it is the case in the known assembly. In order to guarantee the driving force to be transferred and the load-bearing plate 4 to be positioned correspondingly, a specially designed connection arrangement 7 is provided between the reference plate 6 and the load-bearing plate 4, which will be explained in more detail further below. The reference parallel kinematics system 5 (which, in the shown special structure, can also be designated as a reference hexapod) is driveless and comprises absolute length measurement devices in the reference legs (or at least length measurement devices that can be referenced), and therefore is capable of an absolute determination of the posture of its nacelle 5a and thus of the reference plate 6 which is rigidly fixed on the nacelle 5a.

The reference parallel kinematics system and the reference plate 6 are constructed such that only smallest forces act upon the reference plate due to the structure. Incidentally, it can be made of an extremely rigid material and/or have high rigidity through a suitable interior structure. Overall, it thus has to be assumed that the reference plate is not subjected to any relevant deformation and guarantees a smoothly running structure of the reference hexapod, and that between the hexapod and the reference plate, a merely insignificant force exchange takes place.

Figure 3:
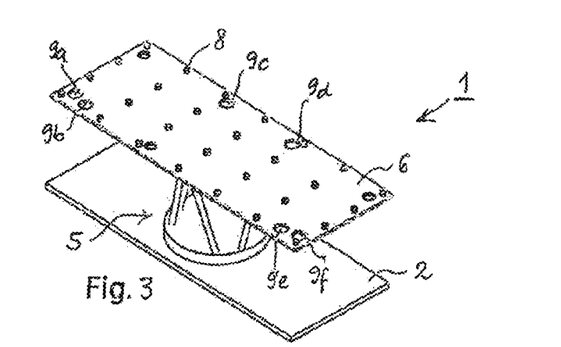

In FIG. 3, the matrix shaped arrangement of distance sensors 8 provided on the upper side of the reference plate 6 can be recognized, by means of which distance sensors, over the entire surface of the load-bearing plate, the respective local distance thereof from the reference plate is detected, and thus the position of the load-bearing plate is detected in a spatially resolved manner. Furthermore, circular openings 9a to 9f having the function described below are shown in FIG. 3. Further details of the reference plate 6 are likewise mentioned and explained further below. Also, as far as the function of the distance sensor system of the assembly according to invention is concerned, more precise explanations can be found further below.

The load-bearing plate is connected to the reference plate in such a manner that a force transfer between the two plates can indeed be suppressed, but at the same time the drive force can be introduced into the load-bearing plate by the drive legs of the drive hexapod 3. For this purpose, the through bores 9a to 9f of the reference plate 9 serve which are designated by 9a to 9f in FIG. 3 but can also be recognized in FIG. 4A (but are not separately designated there). As can be recognized in FIG. 4A, the through bores each are penetrated by one leg shaft 10a to 10f which establish the connection to the drive legs (not shown). The inner diameter of the through bores is selected to be larger relative to the outer diameter of the leg shafts such that no lateral force transmission from the leg shafts to the reference plate will take place under any imaginable operating conditions.

Figure 4A:
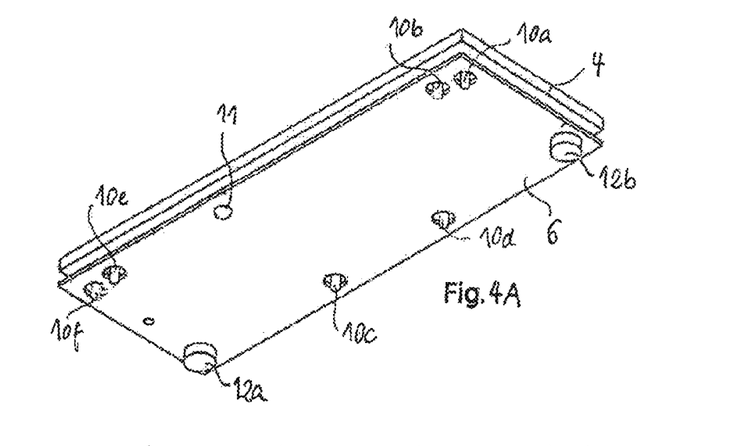
Figure 4B:
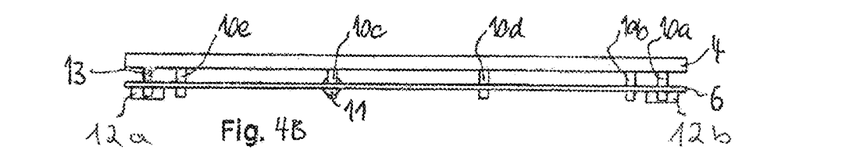
Figure 4C:
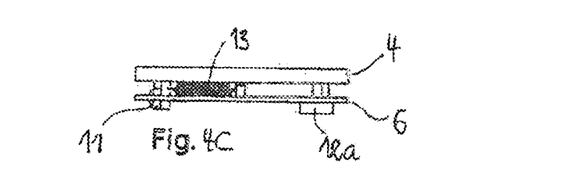

To ensure low-friction contact of the load-bearing plate 4 with the reference plate 6, the load-bearing plate has a ball bearing or ball joint 11 close to one of the long side edges and in a central area thereof, as well as two slide bearings 12a, 12b close to the end points of the opposite side edge. The resting points thus form a large triangle, which provides for a stable support, and due to the low-friction bearings arranged there, this support is largely frictionless.

The ball joint 11 basically enables a relatively slight rotation of the bearing plate 4 with respect to the reference plate 6. In order to counteract such a rotation, a restoring spring device 13 is mounted in the intermediate space between both plates. The restoring spring device 13, for example, comprises a coil spring, the one end of which is wound around one of the leg shafts, and the other end of which is attached to a pin on the surface of the reference plate. A stop plate (not shown) likewise attached to the reference plate rests against another one of the penetrating leg shafts and delimits the action of the restoring spring device.

Figure 5:
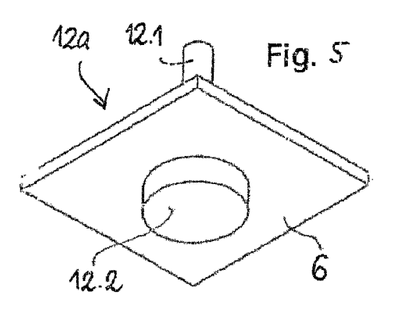

FIG. 5 schematically shows the structure of the slide bearing 12a, which is formed by a circular disc 12.2 mounted on a shaft 12.1, on the upper side of which circular disc the reference plate 6 (symbolized here by a small square plate) is supported.

Figure 6:
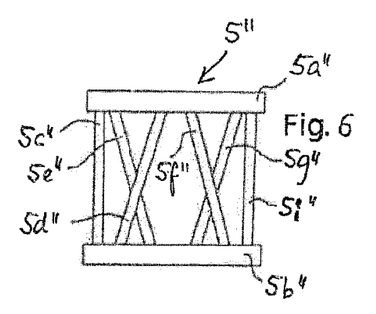
Figure 7:
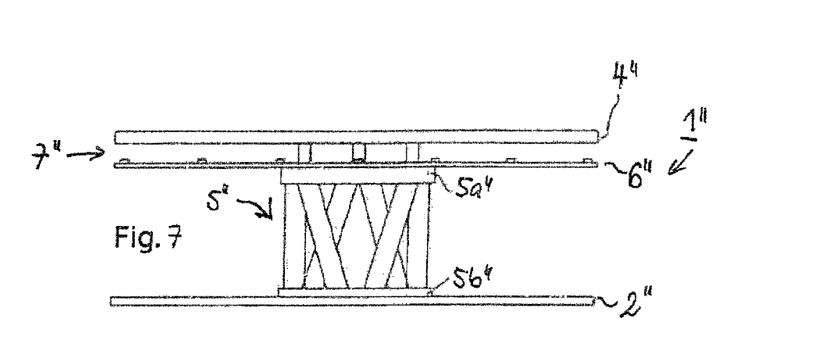
Figure 8:
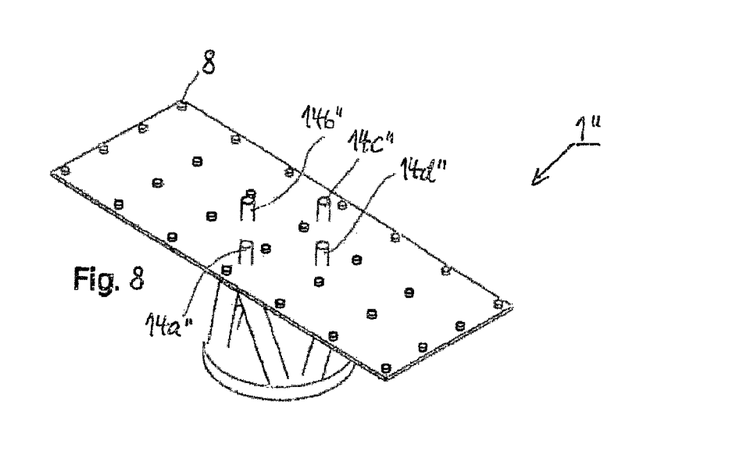

FIGS. 6 to 8 show essential aspects of a further assembly 1" according to the invention. In this assembly 1", a hexapod 5" is installed as the reference parallel kinematics system, which, apart from the nacelle 5a" also has a base plate 5b" of its own, as is illustrated separately in FIG. 6. There, the reference legs are also designated by the numerals 5c" to 5i". Since the structure of the assembly 1" is otherwise similar to that of the assembly 1 from FIGS. 2A to 3, reference numerals based on the first exemplary embodiment are assigned for designating the individual parts. Basically, only the distance sensors 8 are completely unmodified.

While in the first exemplary embodiment above, the drive system and the spatial position or position measurement system, i.e. the driving parallel kinematics system with the load-bearing plate, on the one hand, and the reference parallel kinematics system with the reference plate, on the other, are mechanically separated, this separation is no longer given in the assembly according to FIG. 2. 6 to 8, resulting in a simpler and more cost-efficient construction.

The hexapod 5" here serves the purpose of both driving the load-bearing plate and measuring in a spatially resolved manner the spatial position of the individual points or regions thereof. The legs 5c" to 5f" thus are equipped both with length measurement devices and with drives (not shown). The nacelle 5a" here is fixedly connected to the load-bearing plate 4", for which purpose the four connecting pins 14a" to 14d" that can be recognized in FIG. 8 are provided on the reference plate 6" (which, in turn, is fixedly connected to the nacelle 5a").

Figure 9:
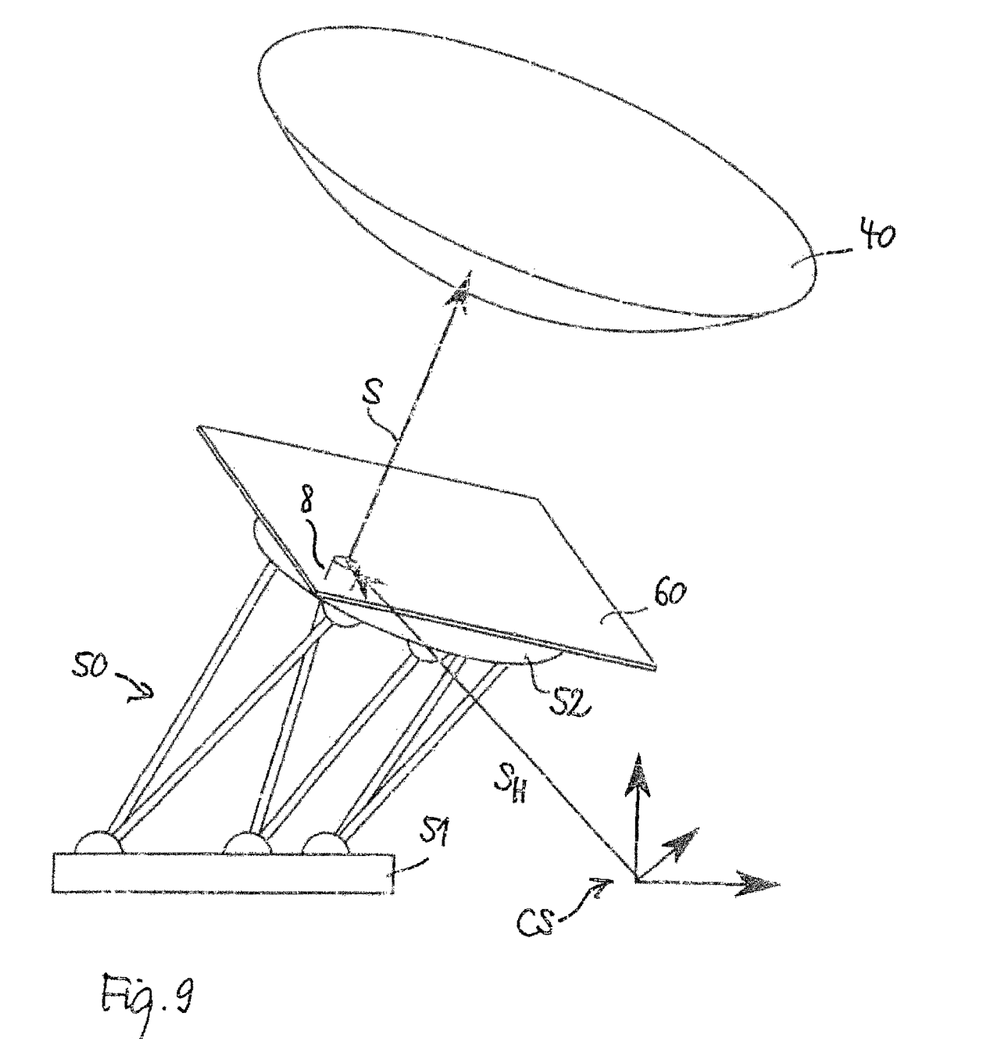
Figure 10A:
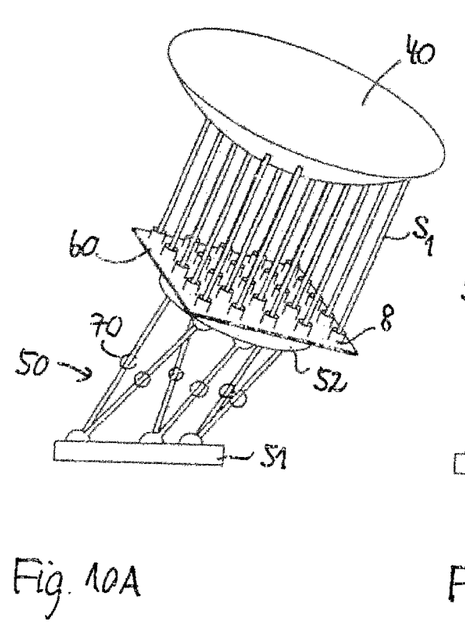
Figure 10B:
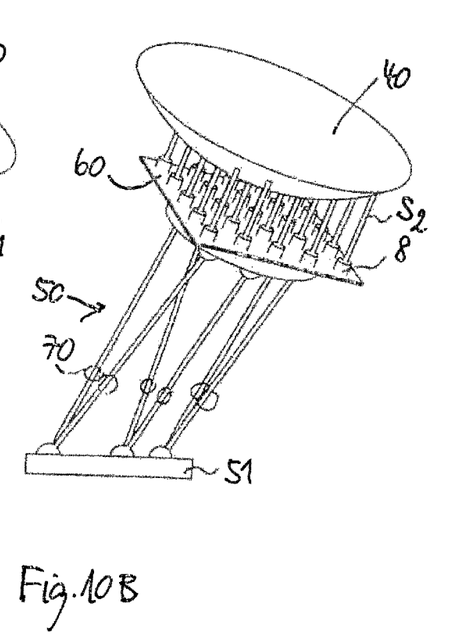

FIGS. 9, 10A and 10B are schematical perspective representations for explaining the functional principle of the (absolute) distance measurement between the reference plate and the load-bearing plate in the assemblies described further above. For differentiating those specific exemplary embodiments, other reference numerals are selected for the schematic representations, which are nevertheless based on the numerals in the exemplary realizations.

As the driving/measuring parallel kinematics system, here again a hexapod 50 is shown, the base plate of which is designated by 51 and the nacelle of which is designated by 52. The reference plate here is designated by the numeral 60, above which a general body 40 in the shape of a flat ball segment is plotted. The lower surface thereof is impinged, as designated by the arrow S in FIG. 9, by a distance sensor 8 having a tightly limited measuring beam.

The direction of the arrow S is in parallel to the surface normal of the reference plate 60, and the length of the arrow (vector) S represents the absolute value measured by the distance sensor 8. The foot point of the vector S is the mounting point of the distance sensor 8, and the coordinates thereof with respect to the reference hexapod coordinate system CS are known since they result from the posture of the hexapod. The surface normal of the reference plate, i.e. the direction of the vector S, also results from this posture. The Cartesian spatial coordinates of the end point of the vector S are given by the vector sum of the vector S and the vector SH between the origin of the reference hexapod coordinate system CS and the foot point of the distance sensor 8.

An essential result of this measuring process is the determination of the spatial coordinates of single surface points of the load-bearing plate in the coordinate system of the reference hexapod CS. The amount of the thus identified spatial (three-dimensional) coordinates of surface points in the coordinate system CS, i.e. the position map, describes the position of the load-bearing plate in space. Due to a connection arrangement according to exemplary embodiment 1 or the construction according to exemplary embodiment 2, the reference plate and the load-bearing plate are shifted relative to one another only in parallel and in the same direction, so that an allocation of surface points of the reference plate and the load-bearing plate, respectively is given in addition.

It should be expressly stated that the posture of the reference plate is required for calculating the mentioned coordinates but is not suitable for describing the position of the load-bearing plate in space. It is an idea of the invention that in each possible class of connection arrangements of the load-bearing plate and the reference plate according to exemplary embodiment 1 deformations of the load-bearing plate result in posture changes of the reference plate so that the posture of the reference plate itself can be considered as being subordinate and consequently can only give rough information on the position of the load-bearing plate in space. It is a further idea of the invention that the posture of the reference plate in an assembly according to exemplary embodiment 2 substantially reflects the position and orientation of a limited surface piece of the load-bearing surface and consequently can likewise only give rough information on the position of the load-bearing plate in space.

In the exemplary embodiments, it is assumed that the optional base plate of the reference hexapod or of the reference parallel kinematics system rests upon an inflexible and rigid foundation, consequently is not subjected to deformation, and the lower coordinates of the reference leg hinge points thus do not experience any shifting, since otherwise no fixed reference coordinate system CS exists. This condition is fulfilled, for example, when the base plate of the load hexapod is founded in this was and the base plate of the reference hexapod is anchored onto it.

FIGS. 10A and 10B exemplify the assembly represented in FIG. 9 in two different positions of the reference plate 60, on the one hand with relatively widely retracted legs of the hexapod 50 (FIG. 10A), and, on the other, with relatively widely extended legs, with the reference plate having been moved into the direction of its surface normal. In these Figures, all of the distance sensors 8 on the reference plate 60 are shown, and one of the measuring beams thereof is designated by way of example by $S_1$ (FIG. 10A) and $S_2$ (FIG. 10B), respectively.

Based on the absolute measurement outlined in FIG. 9 and explained further above, the same coordinates of the corresponding surface points of the lower surface of the body 40 are determined in the coordinate system CS in both positions of the reference plate, although the respective distances between the reference plate 60 and the body 40 are significantly different. From this, it results in turn that the specific position of the reference plate (which is subjected to changes by varying loads of the load-bearing plate) in case of parallel shifting relative to the surface normal at most has a negligible influence on the accuracy of the position map obtained from the load-bearing plate of the assembly—provided that the accuracy of the leg length measurement devices accommodated within the hexapod legs is broadly comparable to that of the distance sensors.

In case of an additional tilting of the reference plate— which in practice is always slight and has no consequence due to the small distance between the reference plate and the load-bearing plate—coordinates of other surface points would be measured, which to a minor extent are laterally shifted relative to the original surface points. However, it is also true here that the spatial coordinates of these new surface points are correctly determined in the coordinate system CS.

In FIGS. 10A and 10B, length measurement devices 70 are symbolically represented in the legs of the hexapod 50, which have already been explained further above. These length measurement devices in hexapod legs are known per se and therefore are not further described here. Apart from the distance sensors 8, they supply the data used for the spatially resolved position determination of the body 40 (or, in practice, of the load-bearing plate).

Within the meaning of the above explanations to FIG. 9, this is data entering into the determination of the end point of the vector SH, and thus finally into the vector sum of the vectors S and SH. It is easy to understand that the leg length data in the postures shown by way of example in FIGS. 10A and 10B, and thus also the corresponding vectors SH to the foot points of the individual distance sensors are different. But the vector addition to the respective likewise different distance vectors results in matching vector sums for both Figures.

The realization of the invention is not restricted to the examples described above and the highlighted aspects, but a great number of modifications is likewise possible, which are within the protective scope of the attached claims and within the scope of expert action.

The invention claimed is:

1. An assembly (1; 1") for the positioning and position detection of a deformable load-bearing plate, having:
   a driving parallel kinematics system (3; 5"; 50) with a plurality of drive legs, wherein the load-bearing plate (4; 4"; 40) forms a constituent part of the driving parallel kinematics system or is fixed rigidly on a platform thereof,
   a reference parallel kinematics system (5; 5"; 50) with a substantially deformation-free reference plate (6; 6"; 60) which is formed by the platform (5a, 5a"; 52) of the reference parallel kinematics system or is fixed rigidly thereto and which is positioned underneath the load-bearing plate, and with a plurality of reference legs, a sensor assembly (8; 70) which comprises a plurality of leg length measurement devices (70) arranged in the reference legs as well as a plurality of distance sensors (8) arranged on the reference plate for point-wise or region-wise detection of the distance of the reference plate from the load-bearing plate, and a position calculating unit which is connected at an input side to the leg length measurement devices and to the distance sensors and which processes the output signals of the leg length measurement devices and distance sensors to give a position map of the load-bearing plate.

2. The assembly according to claim 1, wherein the reference parallel kinematics system is provided as a separate constructional unit (5) in addition to the driving parallel kinematics system (3), and the platform (5*a*) is formed as a load-free platform.

3. The assembly according to claim 2, comprising means for laterally aligning the reference plate with respect to the platform of the driving parallel kinematics system.

4. The assembly according to claim 1, wherein the reference parallel kinematics system (5") is simultaneously formed by the driving parallel kinematics system, wherein the platform (5*a*") of the driving parallel kinematics system is significantly smaller than the load-bearing plate, and consequently is to be considered to be approximately free from deformation.

5. The assembly according to claim 4, wherein the reference plate (6") is provided as an additional element to the platform (5*a*") of the driving/reference parallel kinematics system (5") and is fixedly connected both to the platform of the parallel kinematics system and the load-bearing plate (4").

6. The assembly according to claim 1, wherein the driving parallel kinematics system (3; 5", 50) and/or the reference parallel kinematics system (5; 5", 50) has a hexapod which comprises at least six length-variable legs, which form the drive legs and/or the reference legs, and a nacelle (5*a*; 5*a*"; 52) as a platform.

7. The assembly according to claim 6, wherein the driving parallel kinematics system comprises more than six length-variable drive legs, wherein each of the more than six drive legs is a redundant drive leg.

8. The assembly according to claim 6, wherein the reference parallel kinematics system comprises more than six reference legs, with leg length measurement devices being provided in each of the reference legs.

9. The assembly according to claim 7, wherein at least one redundant drive leg of the driving parallel kinematics system has a force measurement device.

10. The assembly according to claim 1, wherein the leg length measurement devices (70) in the reference legs of the reference parallel kinematics system (5; 5", 50) and the distance sensors (8) on the reference plate (6; 6"; 60) are absolute value sensors.

11. The assembly according to claim 1, wherein the distance sensors (8) are arranged at the corner points of at least one equilateral triangle or rectangle.

12. The assembly according to claim 1, wherein the distance sensors (8) on the reference plate (6; 6"; 60) are arranged to be position-variable such that the position thereof is adjustable in coordination with mechanical properties of the load-bearing plate (4, 4"; 40).

13. The assembly according to claim 1, wherein the load-bearing plate (4, 4"; 40) is formed as a patient table of a medical diagnostic or therapy system.

14. The assembly according to claim 1, wherein the load-bearing plate (4, 4"; 40) is formed as a heavy load platform as part of a technical measurement and processing system.

15. The assembly according to claim 1, having a position tracking unit connected to the output of the position calculating unit at the input side which receives data representing the processing map of the load-bearing plate, and based on the data causes a position tracking of the load-bearing plate in a loaded and deformed state thereof or of a processing, diagnostic or therapy tool of a processing, diagnostic or therapy arrangement.

16. The assembly according to claim 15, wherein the position tracking unit has at least one output connected to at least one of the drive legs of the driving parallel kinematics system for length variation thereof.

17. The assembly according to claim 3, wherein the means for laterally aligning the reference plate with respect to the platform of the driving parallel kinematics system comprise interacting slide agents at the reference plate and the platform of the driving parallel kinematics system, and a laterally acting tension spring device.

18. The assembly according to claim 6, further comprising a base plate (2; 2"; 51).

19. The assembly according to claim 11, wherein the distance sensors (8) are arranged at the corner points of the at least one equilateral triangle or rectangle in an arrangement formed of a plurality of equilateral triangles or rectangles.

\* \* \* \* \*